(12) United States Patent
Shimada et al.

(10) Patent No.: US 8,915,843 B2
(45) Date of Patent: Dec. 23, 2014

(54) LIGHT SOURCE APPARATUS FOR ENDOSCOPE AND CONTROL METHOD FOR LIGHT SOURCE APPARATUS FOR ENDOSCOPE

(71) Applicant: Olympus Medical Systems Corp., Tokyo (JP)

(72) Inventors: Atsushi Shimada, Hachioji (JP); Tomoya Takahashi, Hachioji (JP); Takahiro Masaki, Kawasaki (JP); Mutsumi Oshima, Hachioji (JP); Yasukazu Kogen, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/095,165

(22) Filed: Dec. 3, 2013

(65) Prior Publication Data
US 2014/0139145 A1 May 22, 2014

Related U.S. Application Data

(63) Continuation of application No. PCT/JP2012/080563, filed on Nov. 27, 2012.

(30) Foreign Application Priority Data

Dec. 8, 2011 (JP) ................ 2011-269371

(51) Int. Cl.
*A61B 1/06* (2006.01)
*H05B 37/02* (2006.01)

(52) U.S. Cl.
CPC ............ *H05B 37/02* (2013.01); *H05B 37/0281* (2013.01); *Y02B 20/42* (2013.01)
USPC ........... 600/178; 600/118; 600/180; 600/182; 315/149; 315/156; 315/307; 315/360; 315/361

(58) Field of Classification Search
CPC .... A61B 1/00006; A61B 1/0684; A61B 1/06; A61B 1/0661; A61B 1/07
USPC .......... 600/118, 178, 180, 182; 315/149, 156, 315/307, 361
See application file for complete search history.

(56) References Cited

U.S. PATENT DOCUMENTS

| | | | |
|---|---|---|---|
| 5,868,666 A * | 2/1999 | Okada et al. | 600/118 |
| 6,320,331 B1 * | 11/2001 | Iida et al. | 315/293 |
| 2002/0045801 A1 * | 4/2002 | Niida et al. | 600/118 |

FOREIGN PATENT DOCUMENTS

| | | |
|---|---|---|
| JP | 10-154589 A | 6/1998 |
| JP | 11-204271 A | 7/1999 |
| JP | 2003-131324 A | 5/2003 |
| JP | 2004-031283 A | 1/2004 |
| JP | 2011-124109 A | 6/2011 |

OTHER PUBLICATIONS

International Search Report dated Feb. 5, 2013 issued in PCT/JP2012/080563.

* cited by examiner

*Primary Examiner* — Douglas W Owens
*Assistant Examiner* — Thai Pham
(74) *Attorney, Agent, or Firm* — Scully, Scott, Murphy & Presser, P.C.

(57) ABSTRACT

A light source apparatus for an endoscope, which has a lamp, a power source, a light adjustment control module that controls power to be supplied to the lamp within a range not more than an upper limit power based on a brightness instruction signal, and a continuous lighting sensing module that measures a continuous lighting time period from time when the lamp shifts from being extinguished to being lighted, compares the continuous lighting time period with a predetermined upper limit time period, and initializes the continuous lighting time period while the lamp is extinguished, wherein the upper limit power is set to a first upper limit power when the continuous lighting time period has not reached the upper limit time period, and changed to a second upper limit power lower than the first upper limit power in a stepwise manner when the upper limit time period has not been reached.

2 Claims, 13 Drawing Sheets

FIG.10

| | LIGHTING STATE | |
|---|---|---|
| WHEN CONNECTED | ON | OFF |
| WHEN UNCONNECTED | OFF | OFF |
| WHEN CONNECTED AGAIN | ON | OFF |

FIG.11

| | LIGHTING STATE | |
|---|---|---|
| WHEN CONNECTED | ON | OFF |
| WHEN UNCONNECTED (WITH ON OPERATION) | OFF ↓ ON | OFF ↓ ON |
| WHEN CONNECTED AGAIN | ON | ON |

LIGHT SOURCE APPARATUS FOR ENDOSCOPE AND CONTROL METHOD FOR LIGHT SOURCE APPARATUS FOR ENDOSCOPE

CROSS REFERENCE TO RELATED APPLICATION

This application is a continuation application of PCT/JP2012/080563 filed on Nov. 27, 2012 and claims benefit of Japanese Application No. 2011-269371 filed in Japan on Dec. 8, 2011, the entire contents of which are incorporated herein by this reference.

BACKGROUND OF INVENTION

1. Field of the Invention

The present invention relates to a light source apparatus for an endoscope which can control an amount of outgoing light from a light source portion in a lighted state and a control method for the light source apparatus for the endoscope.

2. Description of the Related Art

A light source apparatus which supplies light to be applied from a distal end portion of an endoscope (scope) to a subject is provided with a light source portion (hereinafter referred to as a lamp) which generates light. Such a lamp decreases in the amount of emitted light or light emission luminance becomes more unstable as a used time period becomes longer, which creates a need for replacement. Under the circumstances, a technique is proposed for prolonging a life of a lamp as much as possible.

For example, Japanese Patent Application Laid-Open Publication No. 2003-131324 describes a discharge lamp lighting apparatus of a projection type image apparatus which has a plurality of power modes available and shifts to a power mode with lower power consumption according to a continuous lighting time period of the lamp, which is different in field from an endoscope. The continuous lighting time period here refers to a total used time period from when a new lamp starts to be used. A power value in each power mode is a value of power actually supplied to a lamp.

Japanese Patent Application Laid-Open Publication No. 2011-124109 describes an illuminance sensorless illumination control system that gauges a cumulative lighting time period with a timer and, when the cumulative lighting time period reaches a predetermined time period, controls a light adjustment output value to a light adjustment output value determined in consideration of a maintenance factor, which is also different in field from an endoscope. The cumulative lighting time period here refers to a total used time period from when a new light source starts to be used. Note that the technique described in Japanese Patent Application Laid-Open Publication No. 2011-124109 is not intended to prolong a lamp life and is configured to perform control that increases a light adjustment output value in order to compensate for decrease in illuminance due to use-induced degradation (see, e.g., paragraph [0041] and FIGS. 2 to 4 of the publication).

Japanese Patent Application Laid-Open Publication No. 2004-31283 describes a technique for obtaining a cumulative energization time period of a light source and reducing, in a stepwise manner, a driving current for the light source with increase in the cumulative energization time period, which is targeted for a liquid crystal display apparatus or the like and is different in field from an endoscope. The cumulative energization time period here refers to a total used time period from when a new light source starts to be used. The current reduced with the cumulative energization time period is a driving current which is actually supplied to the light source. The publication also describes a technique for increasing or reducing the driving current for the light source according to whether surroundings of the light source are bright or dark. More specifically, the technique switches between a D mode corresponding to daytime and an N mode corresponding to nighttime.

The technique described in each publication described above is a technique for controlling power supplied to a light source according to a total used time period from when a new light source starts to be used.

SUMMARY OF THE INVENTION

A light source apparatus for an endoscope according to one aspect of the present invention comprises: a light source portion that can have a lighted state in which light is generated and an extinguished state in which no light is generated; a power supply portion that supplies power for the light source portion to generate light in the lighted state; an outgoing light amount control portion that controls an amount of outgoing light from the light source portion by controlling power to be supplied to the light source portion by the power supply portion within a range not more than an upper limit power based on an inputted brightness instruction signal; and a continuous lighting sensing portion that measures a continuous lighting time period during which the lighted state is maintained without interruption, from a time point when the light source portion shifts from the extinguished state to the lighted state and senses whether the continuous lighting time period has reached a predetermined upper limit time period, and initializes the continuous lighting time period within a period during which the light source portion is in the extinguished state, wherein the outgoing light amount control portion performs power supply control to the light source portion based on the brightness instruction signal with the upper limit power set to a first upper limit power when the continuous lighting time period is not sensed to have reached the upper limit time period, performs power supply control to the light source portion based on the brightness instruction signal with the upper limit power set to a second upper limit power lower than the first upper limit power when the continuous lighting time period is sensed to have reached the upper limit time period, and performs control to make a change from the first upper limit power to the second upper limit power when the continuous lighting time period is sensed to have reached the upper limit time period in a stepwise manner in decrements each smaller than a power difference between the first upper limit power and the second upper limit power.

A control method for a light source apparatus for an endoscope according to another aspect of the present invention comprises: shifting a light source portion from an extinguished state in which no light is generated to a lighted state in which light is generated by supplying power to the light source portion; measuring a continuous lighting time period during which the lighted state is maintained without interruption, from a time point when the light source portion shifts from the extinguished state to the lighted state; sensing whether the continuous lighting time period has reached a predetermined upper limit time period; controlling power to be supplied to the light source portion based on an inputted brightness instruction signal with an upper limit power which serves as an upper limit for the power to be supplied to the light source portion set to a first upper limit power when the continuous lighting time period is not sensed to have reached the upper limit time period; controlling the power to be supplied to the light source portion based on the brightness instruction signal with the upper limit power that serves as the upper limit for the power to be supplied to the light source portion set to a second upper limit power lower than the first upper limit power when the continuous lighting time period is sensed to have reached the upper limit time period, and controlling a change from the first upper limit power to the second upper limit power when the continuous lighting time period is sensed to have reached the upper limit time period, to be performed in a stepwise manner in decrements each smaller than a power difference between the first upper limit power and the second upper limit power; and initializing the continuous lighting time period within a period during which the light source portion is in the extinguished state.

BRIEF DESCRIPTION OF THE DRAWINGS

FIG. 10 is a chart showing how a lighting state of the lamp changes with change in a state of the scope between connected and unconnected, according to the first embodiment;

FIG. 11 is a chart showing how the lighting state of the lamp changes with change in the state of the scope between connected and unconnected when manual on operation is performed while the scope is unconnected, according to the first embodiment;

DETAILED DESCRIPTION OF THE PREFERRED EMBODIMENT(S)

An embodiment of the present invention will be described below with reference to the drawings.

First Embodiment

Figure 1:
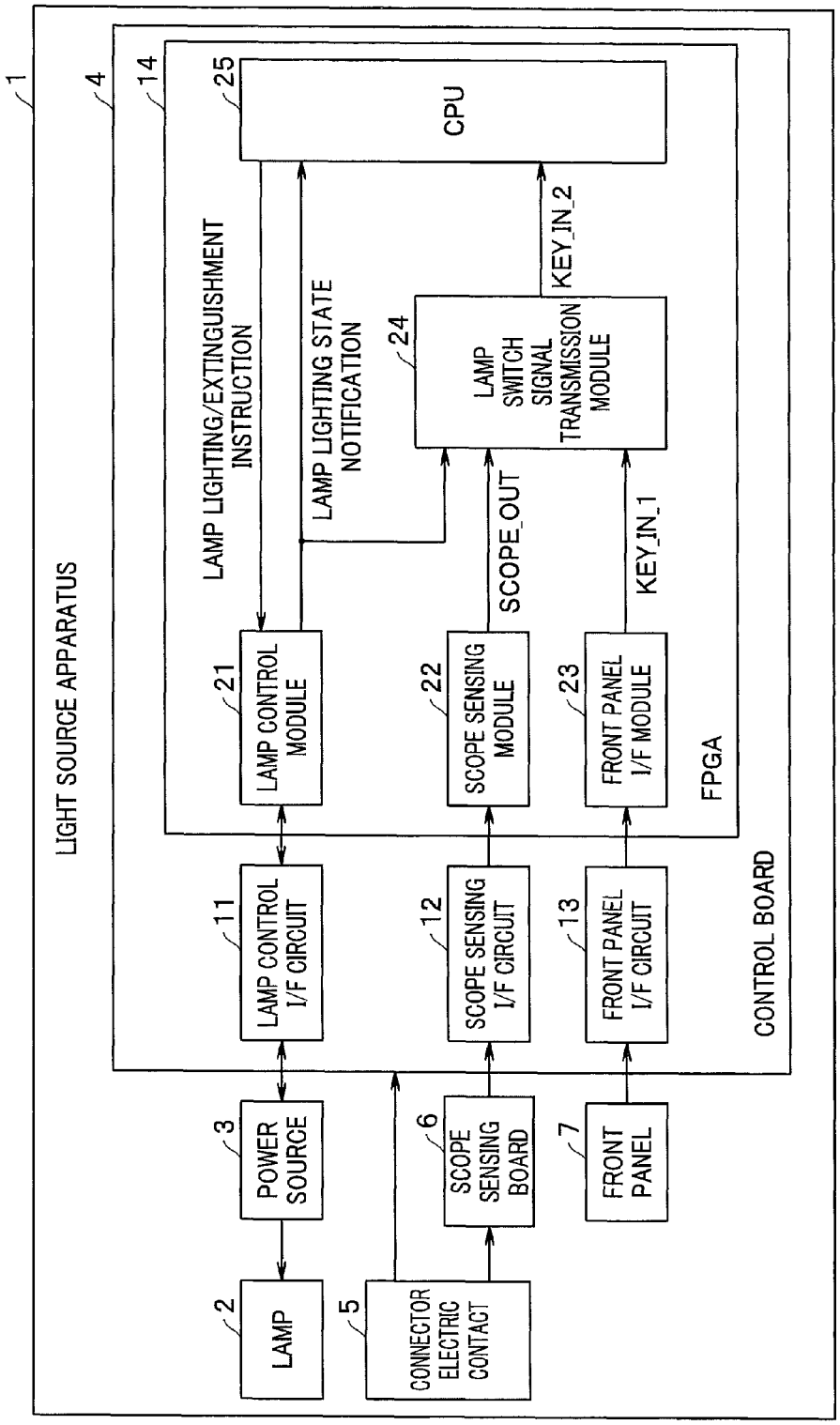
FIG. 1 is a block diagram showing a configuration of a light source apparatus according to a first embodiment of the present invention.

FIGS. 1 to 21 show a first embodiment of the present embodiment. FIG. 1 is a block diagram showing a configuration of a light source apparatus.

A light source apparatus 1 is an apparatus which supplies light for illumination to a scope (endoscope) 100 (see FIG. 8) when the light source apparatus 1 is connected to the scope 100 and includes a lamp 2, a power source 3, a control board 4, a connector electric contact 5, a scope sensing board 6, and a front panel 7.

The lamp 2 is a light source portion which can have a lighted state in which light is generated and an extinguished state in which no light is generated.

The power source 3 is a power supply portion which supplies power for the lamp 2 to generate light in the lighted state.

The connector electric contacts 5 are disposed in an output connector 47 (see FIGS. 7 to 9), to which the scope 100 is to be connected. Electric contacts on the scope 100 side are electrically connected to the connector electric contacts 5 (see also FIGS. 12 to 17).

The scope sensing board 6 is a board which senses whether the scope 100 is connected via the connector electric contacts 5. Note that although sensing utilizing the connector electric contacts 5 is performed here, the present invention is not limited thereto. Connection sensing may be mechanically performed or may be performed by using a sensor or the like.

Figure 7:
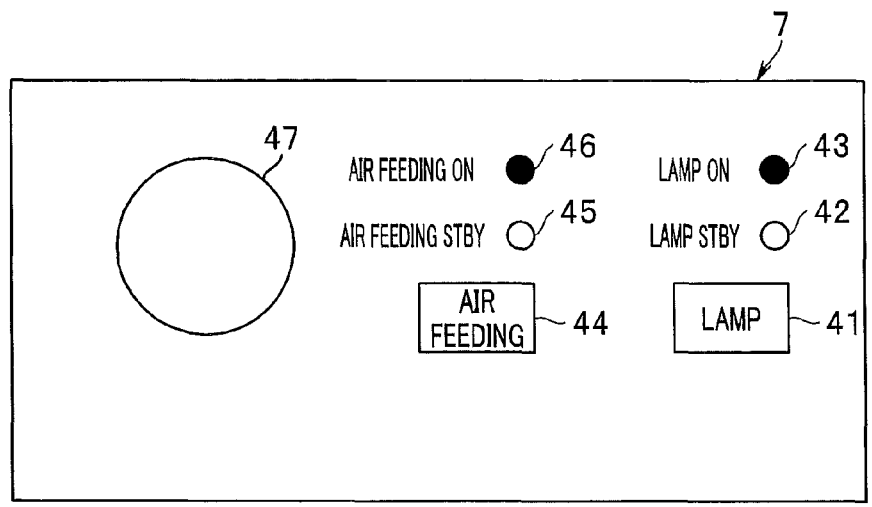
FIG. 7 is a view showing display on a front panel when the light source apparatus is in an air feeding stopped state and a lamp extinguished state, according to the first embodiment.
Figure 8:
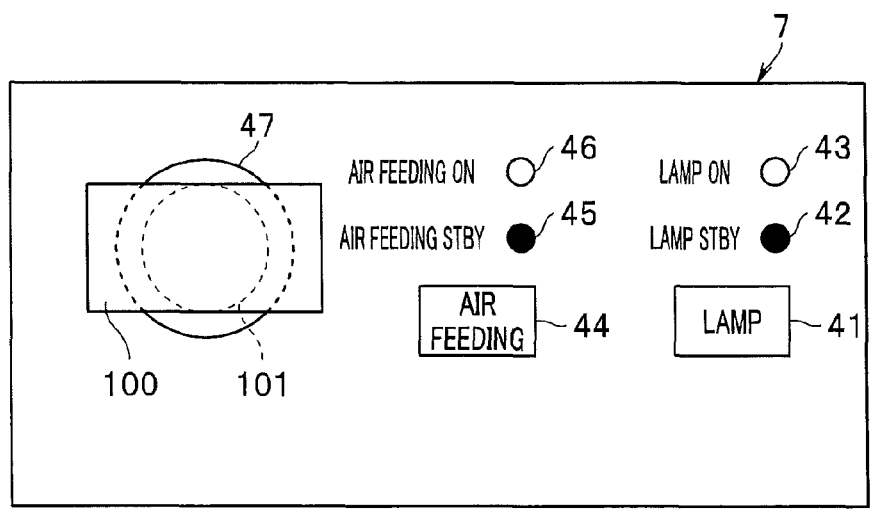
FIG. 8 is a view showing display on the front panel when a scope is connected, and the light source apparatus is in an air feeding driven state and a lamp lighted state, according to the first embodiment.
Figure 9:
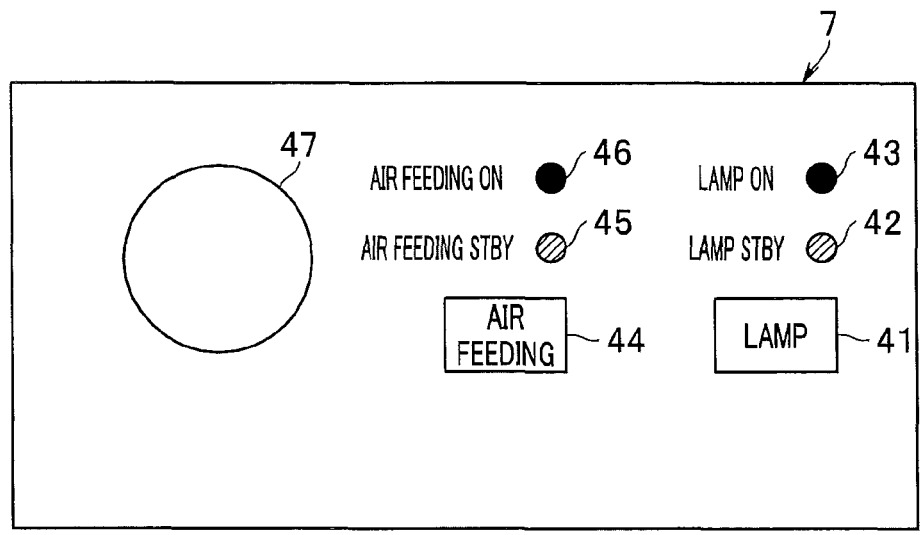
FIG. 9 is a view showing display on the front panel when the scope is unconnected, and the light source apparatus is to enter the air feeding driven state and the lamp lighted state when the scope is connected, according to the first embodiment.

The front panel 7 is for giving operation input to the light source apparatus 1 and performs, e.g., display of a state of the light source apparatus 1 (see also FIGS. 7 to 9).

The control board 4 controls turn-on/off of power supplied to the lamp 2 by the power source 3 or a power value according to a result of sensing by the scope sensing board 6 and an operation input from the front panel 7.

The control board 4 includes a lamp control I/F circuit 11, a scope sensing I/F circuit 12, a front panel I/F circuit 13, and a FPGA (field programmable gate array) 14.

The lamp control I/F circuit 11 is an interface circuit between the FPGA 14 and the power source 3.

The scope sensing I/F circuit 12 is an interface circuit between the FPGA 14 and the scope sensing board 6.

The front panel I/F circuit 13 is an interface circuit between the FPGA 14 and the front panel 7.

The FPGA 14 is a programmable LSI (large scale integration) which is composed of modules for performing lamp control on the basis of a scope sensing result and an operation input, and the like.

The FPGA 14 includes a lamp control module 21, a scope sensing module 22, a front panel I/F module 23, a lamp switch signal transmission module 24, and a CPU 25.

The scope sensing module 22 outputs a signal SCOPE_OUT indicating whether the scope 100 is connected to the lamp switch signal transmission module 24 on the basis of an input from the scope sensing I/F circuit 12.

The front panel I/F module 23 outputs a signal KEY_IN_1 indicating whether a lamp switch 41 (see, e.g., FIGS. 7 to 9) for manual operation for lighting/extinguishment of the lamp 2 is on to the lamp switch signal transmission module 24 on the basis of an input from the front panel I/F circuit 13.

The lamp switch signal transmission module 24 outputs a signal KEY_IN_2 to the CPU 25 on the basis of the signal SCOPE_OUT from the scope sensing module 22, the signal KEY_IN_1 from the front panel I/F module 23, and a lamp lighting state notification signal from the lamp control module 21. The lamp switch signal transmission module 24 outputs the signal KEY_IN_1 as the signal KEY_IN_2 to the CPU 25 without change or outputs a dummy signal different from the signal KEY_IN_1 as the signal KEY_IN_2 to the CPU 25, according to a mode setting on the light source apparatus 1 and each input signal. A lighting state of the lamp 2 based on the signal KEY_IN_2 outputted by the lamp switch signal transmission module 24 will be described later with reference to FIGS. 10 and 11.

The CPU 25 controls the whole light source apparatus 1. The CPU 25 is configured to accept the signal KEY_IN_2 and output, to the lamp control module 21, a lamp extinguishment instruction signal if the lamp is lighted and a lamp lighting instruction signal if the lamp is extinguished. The lamp lighting state notification signal is sent from the lamp control module 21 to the CPU 25.

The lamp control module 21 receives the lamp lighting/extinguishment instruction signal from the CPU 25, outputs a control signal corresponding to the received instruction signal to the lamp control I/F circuit 11, and executes lighting/extinguishment of the lamp 2. Additionally, the lamp control module 21 includes a light adjustment control module 33 (see FIG. 2) which is an outgoing light amount control portion that controls the amount of outgoing light from the lamp 2 by controlling power supplied from the power source 3 to the lamp 2 within a range equal to or not more than a predetermined upper limit power.

Figure 5:
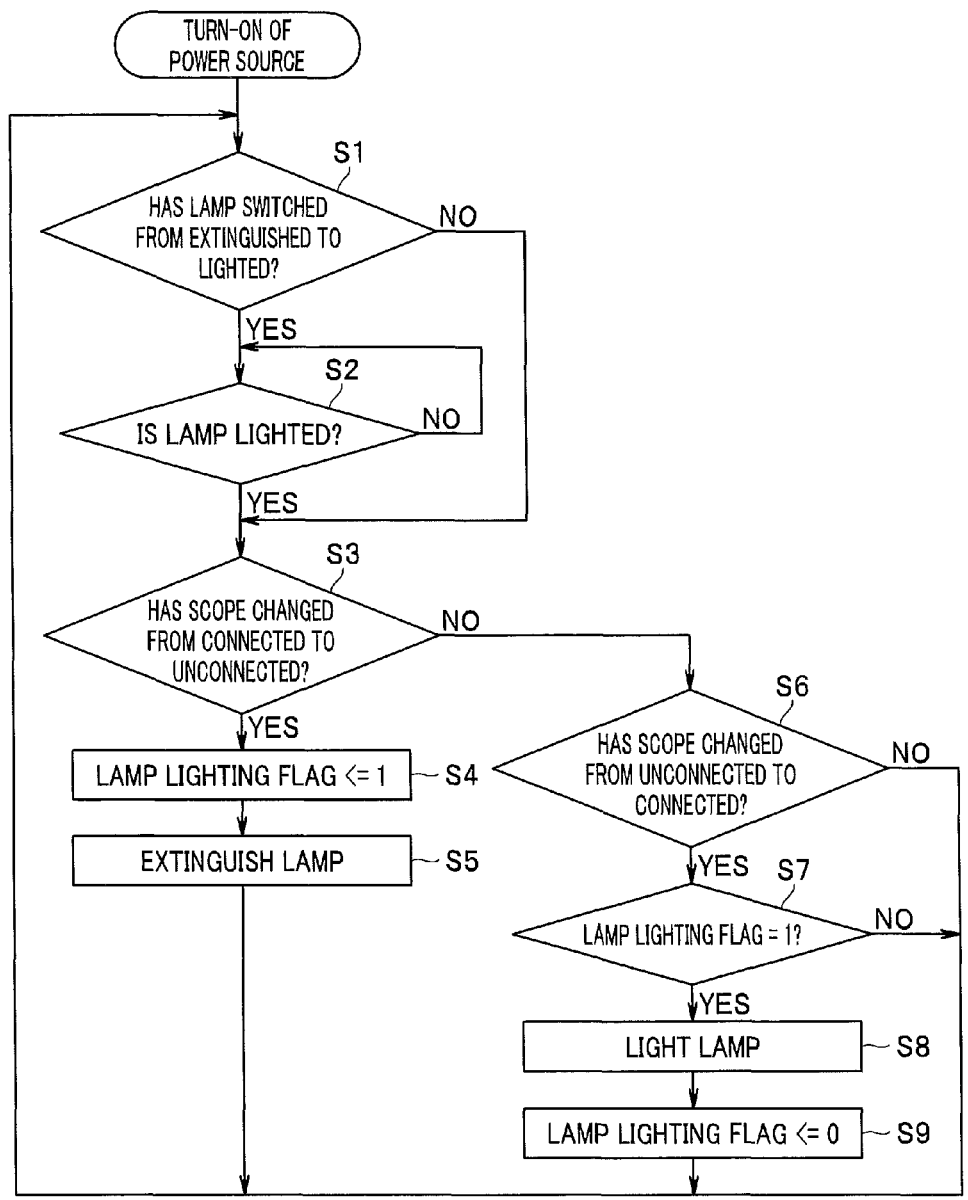
FIG. 5 is a flowchart showing lamp lighting/extinguishment control of the light source apparatus according to the first embodiment.

Lamp lighting/extinguishment control of the whole light source apparatus 1 will first be described with reference to FIG. 5. FIG. 5 is a flowchart showing the lamp lighting/extinguishment control of the light source apparatus 1.

When the power source of the light source apparatus 1 is turned on, the process is started. When the signal KEY_IN_2 inputted from the lamp switch signal transmission module 24 to the CPU 25 while the lamp is extinguished is inputted to the CPU 25, the CPU 25 outputs a lamp lighting instruction signal to the lamp control module 21 to switch the lamp from extinguished to lighted. The lamp control module 21 detects whether the lamp has changed from extinguished to lighted (step S1).

If it is detected in step S1 that the lamp has changed from extinguished to lighted, the CPU 25 waits for a state notification signal indicating that the lamp is lighted to be inputted from the lamp control module 21 (step S2).

When the lamp lighting state notification signal is inputted or if it is not detected in step S1 that the lamp has changed from extinguished to lighted, the lamp switch signal transmission module 24 determines whether the scope 100 is removed and has changed from a connected state to an unconnected state (step S3).

If it is determined on the basis of acceptance of a signal of scope change from connected to unconnected from the scope sensing board 6 by the FPGA 14 that the signal SCOPE_OUT has changed from a signal indicating that the scope 100 is connected to a signal indicating that the scope 100 is unconnected, the lamp switch signal transmission module 24 sets an internal lamp lighting flag to 1 (the symbol "<=" in FIG. 5 represents setting a value; the same applies hereinafter) (step S4) and sends the signal KEY_IN_2 for extinguishing the lamp to the CPU 25.

Upon receipt of the signal KEY_IN_2, the CPU 25 transmits a lamp extinguishment instruction signal to the lamp control module 21. The lamp control module 21 instructs the power source 3 to extinguish the lamp, and the lamp 2 is extinguished (step S5).

Note that the lamp lighting flag is set to 1 in step S4 to make clear that the lamp 2 is to be lighted this time by viewing the lamp lighting flag when the lamp 2 is changed again between lighted and extinguished after the lamp 2 is extinguished in step S5.

If it is determined in step S3 that the scope 100 has not changed from the connected state to the unconnected state, it is determined whether the scope 100 is attached and has changed from the unconnected state to the connected state (step S6).

If it is determined on the basis of acceptance of a signal of scope change from unconnected to connected from the scope sensing board 6 by the FPGA 14 that the signal SCOPE_OUT has changed from the signal indicating that the scope 100 is unconnected to the signal indicating that the scope 100 is connected, the lamp switch signal transmission module 24 determines whether the internal lamp lighting flag is 1 (step S7).

If it is determined that the lamp lighting flag is not 1 (i.e., is 0), the state of the lamp 2 is maintained without change.

On the other hand, if it is determined that the lamp lighting flag is 1, the lamp switch signal transmission module 24 sends the signal KEY_IN_2 for lighting the lamp to the CPU 25. Upon receipt of the signal KEY_IN_2, the CPU 25 sends a lamp lighting instruction signal to the lamp control module 21. The lamp control module 21 instructs the power source 3 to light the lamp, and the lamp 2 is lighted (step S8).

After the lighting, the lamp switch signal transmission module 24 sets the lamp lighting flag to 0 in preparation for extinguishment of the lamp for next time (step S9).

When the process in step S5 or in step S9 ends, if it is determined in step S6 that the scope 100 has not changed from the unconnected state to the connected state, or if it is determined in step S7 that the lamp lighting flag is not 1 (i.e., is 0), the flow returns to step S1 to repeatedly perform the above-described processes.

According to the above-described process, a loop passing through steps S1 (NO), S3 (NO), and S6 (NO) (hereinafter referred to as a basic loop) is executed while a connection state of the scope 100 does not change. If the scope 100 changes from connected to unconnected during the basic loop, lamp extinguishment is automatically performed in step S5 without a need for user operation. After the extinguishment, the basic loop is executed in a lamp extinguished state with the lamp lighting flag of 1 set in step S4.

If the scope 100 changes from unconnected to connected during execution of the basic loop, since the lamp lighting flag is set to 1 at the time of automatic lamp extinguishment, lamp lighting is automatically performed in step S8 without a need for user operation. After the lighting, the basic loop is executed in a lamp lighted state with the lamp lighting flag of 0 set in step S9.

Motion when the scope 100 changes again from connected to unconnected during execution of the basic loop is same as described above.

With the process as shown in FIG. 5, lighting/extinguishment of the lamp 2 is automatically performed in response to attachment or detachment of the scope 100, without a need for switching operation by a user.

Note that if switching operation is performed by a user during automatic lighting/extinguishment motion, the user operation is given higher priority depending on the situation. Thus, the lighting state to be realized of the lamp 2 is as shown in FIGS. 10 and 11. FIG. 10 is a chart showing how the lighting state of the lamp changes with change in the state of the scope between connected and unconnected. FIG. 11 is a chart showing how the lighting state of the lamp changes with change in the state of the scope between connected and unconnected when manual on operation is performed while the scope is unconnected.

Assume a case where the lamp 2 is on when the scope 100 is connected, as shown in FIG. 10. When the scope 100 is pulled out and becomes unconnected in the state, the lamp 2 is automatically turned off. When the scope 100 is connected again after the pull-out, the lamp 2 automatically shifts to a state identical to the state when the scope 100 was connected before, i.e., an on state. The processing is realized by the above-described flow in FIG. 5.

Assume a case where the lamp 2 is off when the scope 100 is connected. Even if the scope 100 is pulled out and becomes unconnected in the state, the lamp 2 remains off. When the scope 100 is connected again after the pull-out, the lamp 2 automatically shifts to a state identical to the state when the scope 100 was connected before, i.e., an off state. That is, the scope 100 remains off.

A change in the lighting state when on operation of the lamp switch 41 is manually performed while the scope 100 is unconnected is as shown in FIG. 11.

Assume a case where the lamp 2 is on when the scope 100 is connected. When the scope 100 is pulled out and becomes unconnected in the state, the lamp 2 is automatically turned off. When on operation of the lamp switch 41 is manually performed while the scope 100 is unconnected, the lamp 2 is turned on. Even if the scope 100 is connected again after the on operation, the lamp 2 remains in the on state.

Assume a case where the lamp 2 is off when the scope 100 is connected. Even if the scope 100 is pulled out and becomes unconnected in the state, the lamp 2 remains off. When on operation of the lamp switch 41 is manually performed while the scope 100 is unconnected, the lamp 2 is turned on. Even if the scope 100 is connected again after the on operation, the lamp 2 remains in the on state.

A user often fails to extinguish the lamp 2 of the light source apparatus 1 after completion of an examination using the scope. In the case, the lamp 2 of the light source apparatus 1 remains lighted between a given examination and a next examination, which causes occurrence of wasteful power consumption during a time period when no examination is performed. To cope with the case, the process as shown in FIG. 5 is performed by using the configuration as shown in FIG. 1 to obtain a change in lighting state as shown in the left column of FIG. 10. It is thus possible to automatically perform lighting/extinguishment of the lamp without a user's operation of lighting/extinguishing the lamp and inhibit occurrence of wasteful power consumption.

If a user manually performs an operation of lighting the lamp when the scope 100 is unconnected, a lighting state which pays regard to the user's intention can be obtained, as shown in FIG. 11.

Figure 2:
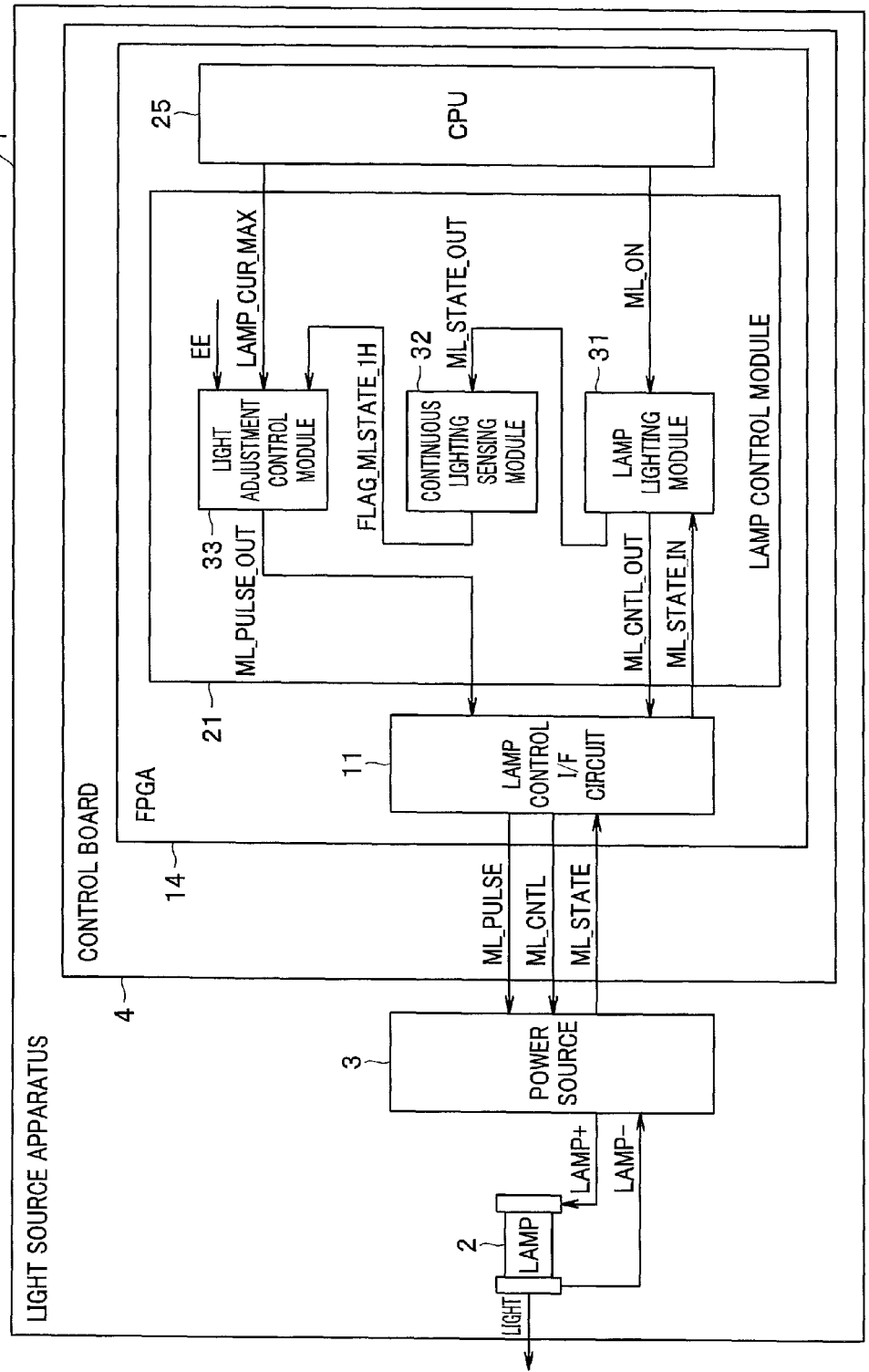
FIG. 2 is a block diagram showing components of the light source apparatus which are associated with lamp luminance control, according to the first embodiment.
Figure 3:
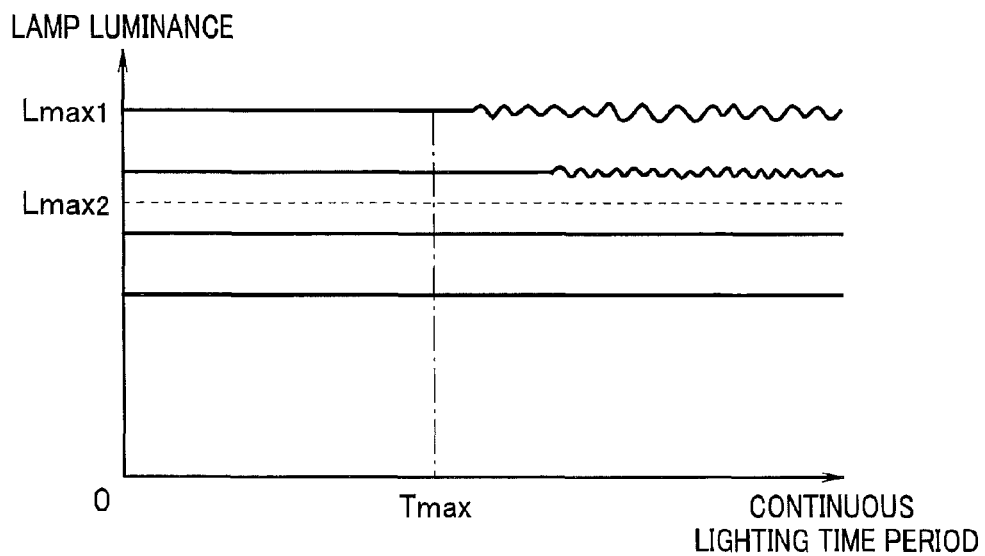
FIG. 3 is a chart showing how lamp luminance is in one continuous lighting task, according to the first embodiment.
Figure 4:
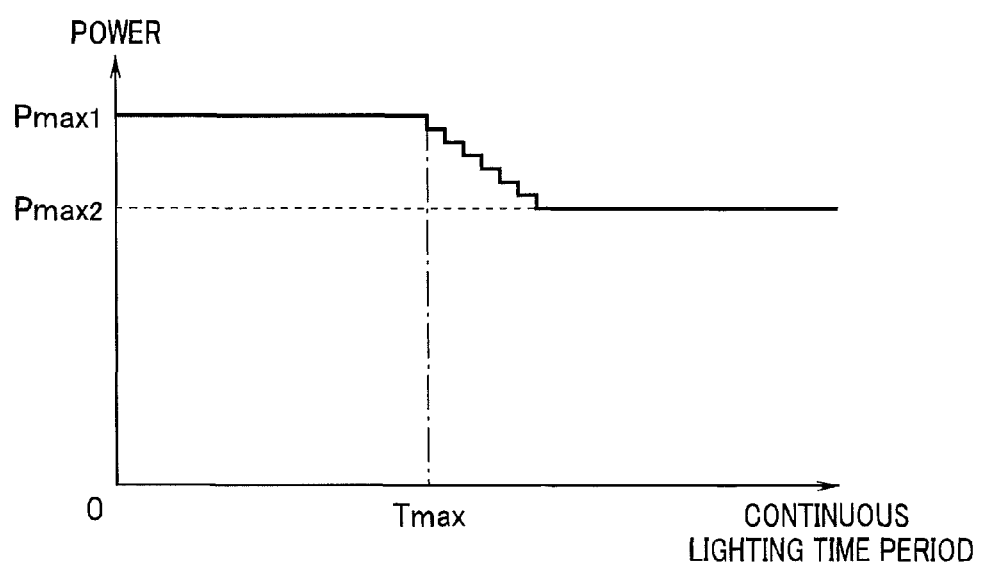
FIG. 4 is a chart showing an example in which power to be supplied to a lamp is changed with time in one continuous lighting task, according to the first embodiment.

FIG. 2 is a block diagram showing components of the light source apparatus which are associated with lamp luminance control. FIG. 3 is a chart showing how lamp luminance is in one continuous lighting task. FIG. 4 is a chart showing an example in which power to be supplied to the lamp is changed with time in one continuous lighting task.

Assume that the lamp 2 continues to be lighted with, for example, maximum luminance Lmax1 during one lighting task. As shown in FIG. 3 and described above, a phenomenon in which light emission luminance of the lamp becomes unstable (or a phenomenon in which a light emission spectrum of the lamp changes; note that, hereinafter, the phenomenon in which the luminance becomes unstable will be taken as a representative hereinafter) starts to be seen at a time point after a continuous lighting time period has exceeded a time period Tmax.

Assume that the luminance of the lamp 2 is made slightly lower than the maximum luminance Lmax1 described above. Although a time point when the light emission luminance of the lamp 2 becomes unstable may be somewhat delayed or a fluctuation range of the luminance may become somewhat narrower, a phenomenon in which the light emission luminance of the lamp 2 becomes unstable is still produced.

In contrast, when the luminance of the lamp 2 is set to be not more than given threshold luminance Lmax2, a phenomenon in which the light emission luminance of the lamp 2 becomes unstable is not practically produced (i.e., the luminance of the lamp 2 remains constant or only negligible fluctuations are produced in the luminance) even if continuous lighting is performed during one lighting task.

For the reason, the configuration shown in FIG. 2 prevents the light emission luminance of the lamp 2 from becoming unstable while securing the maximum luminance of the lamp 2 as much as possible.

As shown in FIG. 2, the lamp control module 21 includes a lamp lighting module 31 that controls lamp lighting/extinguishment, a continuous lighting sensing module 32 that is a continuous lighting sensing portion which senses a continuous lighting time period of the lamp 2, and the light adjustment control module 33 that is an outgoing light amount control portion for controlling a lamp current.

Figure 6:
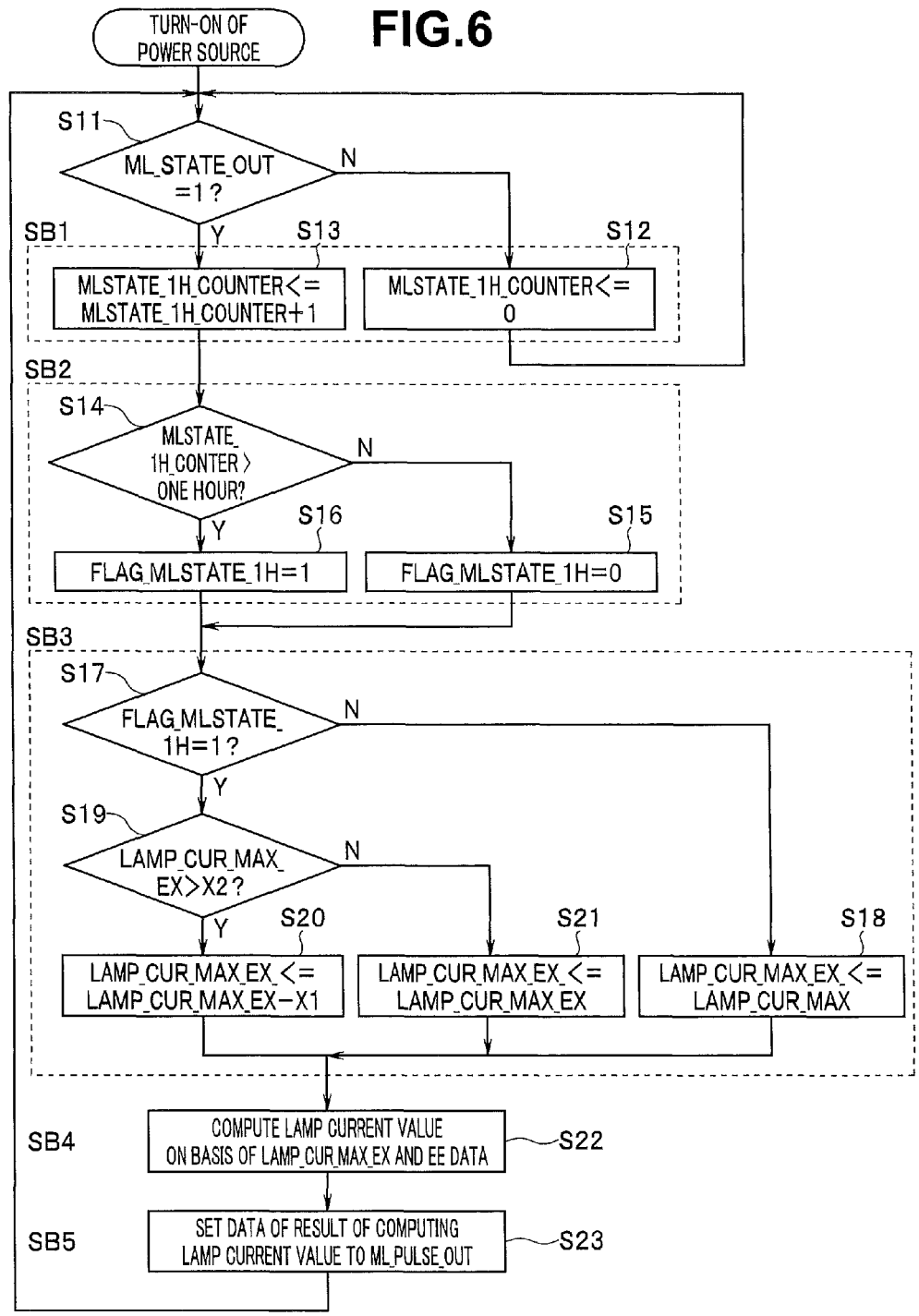
FIG. 6 is a flowchart showing a process of controlling a lamp current during one lighting task, according to the first embodiment.

FIG. 6 is a flowchart showing a process of controlling a lamp current during one lighting task. The process shown in FIG. 6 is performed without interruption after the lamp 2 changes from the extinguished state to the lighted state and while the lighted state is maintained and ends when the lamp 2 shifts again to the extinguished state, in the process shown in FIG. 5. Note that although a case where Tmax shown in FIGS. 3 and 4 is one hour will be described as an example with reference to FIG. 6, Tmax is, of course, set to an appropriate time period according to a manufacturer and the type of a lamp.

When the power source is turned on, the CPU 25 sends LAMP_CUR_MAX (current value data corresponding to the maximum luminance Lmax1 shown in FIG. 3 and a first upper limit power Pmax1 shown in FIG. 4) that is a first upper limit power and is lamp maximum allowable current value data to the light adjustment control module 33. The light adjustment control module 33 stores LAMP_CUR_MAX received from the CPU 25 in an internal buffer LAMP_CUR_MAX_EX.

When on operation of the lamp switch 41 of the front panel 7 is performed or connection of the scope is sensed by the scope sensing board 6 after the storage, the CPU 25 sets ML_ON to 1 and sends ML_ON as a lamp lighting instruction signal to the lamp lighting module 31.

The lamp lighting module 31 outputs ML_CNTL_OUT to the lamp control I/F circuit 11. With ML_CNTL_OUT, the lamp control I/F circuit 11 sets ML_CNTL to 0 and sends ML_CNTL as a lamp lighting instruction to the power source 3.

Upon receipt of the lamp lighting instruction, the power source 3 supplies, for example, voltages between two electrodes, LAMP+ and LAMP− to the lamp 2, and the lamp 2 emits light.

An EE signal which is brightness instruction data is inputted to the light adjustment control module 33 described above from a video processor (not shown). The light adjustment control module 33 generates ML_PULSE_OUT for controlling a lamp current on the basis of various parameters within a range not exceeding a current value corresponding to the value stored in the internal buffer LAMP_CUR_MAX_EX and sends ML_PULSE_OUT to the lamp control I/F circuit 11. Upon receipt of ML_PULSE_OUT from the light adjustment control module 33, the lamp control I/F circuit 11 outputs a signal ML_PULSE for controlling the current to the power source 3. The power source 3 makes the current vary according to the signal ML_PULSE from the lamp control I/F circuit 11 and outputs the current to the lamp 2. Thus, the lamp 2 performs light emission within the range not exceeding the current value corresponding to LAMP_CUR_MAX_EX described above.

Note that, in an initial state after the power source is turned on, LAMP_CUR_MAX sent from the CPU 25 is stored in the internal buffer LAMP_CUR_MAX_EX of the light adjustment control module 33. Thus, the lamp 2 performs light emission within the range not exceeding the current value corresponding to LAMP_CUR_MAX.

When the lamp 2 is lighted, the power source 3 sets ML_STATE to 0, sends ML_STATE to the lamp control I/F circuit 11, and notifies the lamp control I/F circuit 11 that the lamp 2 is lighted.

Upon receipt of a lamp lighting notification, the lamp control I/F circuit 11 sends ML_STATE_IN to the lamp lighting module 31.

Upon receipt of ML_STATE_IN from the lamp control I/F circuit 11, the lamp lighting module 31 outputs ML_STATE_OUT to the continuous lighting sensing module 32.

The continuous lighting sensing module 32 monitors ML_STATE_OUT from the lamp lighting module 31 (step S11). In step block SB1, the continuous lighting sensing module 32 resets (i.e., initializes) an internal counter MLSTATE_1H_COUNTER indicating a continuous lighting time period (step S12) if ML_STATE_OUT is 0 and executes count-up of the internal counter MLSTATE_1H_COUNTER (step S13) if ML_STATE_OUT is 1. In the above-described manner, the continuous lighting sensing module 32 executes count-up of the internal counter MLSTATE_1H_COUNTER while the lamp 2 continues to be lighted (i.e., while ML_STATE_OUT is 1).

In step block SB2, the continuous lighting sensing module 32 monitors a count value of the internal counter MLSTATE_1H_COUNTER to check whether the count value has become a value indicating a lapse of one hour (step S14). The continuous lighting sensing module 32 sets FLAG_MLSTATE_1H to 0 (step S15) if an elapsed time period has not reached one hour and sets FLAG_MLSTATE_1H to 1 (step S16) if the elapsed time period has exceeded one hour. FLAG_MLSTATE_1H is sent from the continuous lighting sensing module 32 to the light adjustment control module 33.

In following step block SB3, the light adjustment control module 33 monitors FLAG_MLSTATE_1H (step S17) to check whether FLAG_MLSTATE_1H inputted from the continuous lighting sensing module 32 is 1, i.e., whether the continuous lighting time period has exceeded one hour.

If the continuous lighting time period has not reached one hour (FLAG_MLSTATE_1H=0), the light adjustment control module 33 continues to cause the internal buffer LAMP_CUR_MAX_EX to store the lamp maximum allowable current value data LAMP_CUR_MAX from the CPU 25 (step S18).

If the continuous lighting time period has exceeded one hour (FLAG_MLSTATE_1H=1), the light adjustment control module 33 determines whether the value stored in the internal buffer LAMP_CUR_MAX_EX is larger than second upper limit current value data X2 (step S19). Note that the second upper limit current value data X2 is current value data corresponding to the threshold luminance Lmax2 shown in FIG. 3 and a second upper limit power Pmax2 shown in FIG. 4 and is current value data lower than the lamp maximum allowable current value data LAMP_CUR_MAX corresponding to the first upper limit power Pmax1. Thus, the second upper limit current value data X2 is lamp current value data which can inhibit the lamp 2 from wearing off (i.e., which prevents production of a flicker and a color shift of the lamp 2) even if one lighting task lasts for a long time period.

If it is determined that the value stored in the internal buffer LAMP_CUR_MAX_EX is larger than the second upper limit current value data X2, the light adjustment control module 33 stores, in the internal buffer LAMP_CUR_MAX_EX, a value obtained by subtracting a predetermined step value X1 from the value presently stored in the internal buffer LAMP_CUR_MAX_EX (step S20). The predetermined step value X1 here is a value which can be obtained by dividing a current value difference between the lamp maximum allowable current value data LAMP_CUR_MAX corresponding to the first upper limit power Pmax1 and the above-described second upper limit current value data X2 into a plurality of steps and corresponds to a power step value of the stepped portion shown in FIG. 4.

On the other hand, if it is determined in step S19 that the value stored in the internal buffer LAMP_CUR_MAX_EX is not larger than the second upper limit current value data X2, the light adjustment control module 33 maintains the value presently stored in the internal buffer LAMP_CUR_MAX_EX without change (step S21).

With the process in step block SB3, if the continuous lighting time period for one time of the lamp 2 exceeds $T_{max}$ (one hour in the above-described example), the light adjustment control module 33 lowers, in a stepwise manner, power supplied to the lamp 2 from the first upper limit power Pmax1 toward the second upper limit power Pmax2, as shown in FIG. 4. The light adjustment control module 33 shifts to a state which prevents occurrence of a flicker and a color shift of the lamp 2 while preventing a change in brightness of light from the lamp 2 from giving an unnatural feeling to a user.

When the process in step block SB3 (more specifically, the process in step S18, S20, or S21) ends, the light adjustment control module 33 computes a value of current supplied to the lamp 2 on the basis of an EE signal which is brightness instruction data from the video processor by using the value stored in the internal buffer LAMP_CUR_MAX_EX as a present upper limit current value in step block SB4 (step S22).

In step block SB5, the light adjustment control module 33 sets a current value as a computation result to ML_PULSE_OUT and outputs ML_PULSE_OUT to the lamp control I/F circuit 11 (step S23). Upon receipt of ML_PULSE_OUT, the lamp control I/F circuit 11 outputs the signal ML_PULSE for controlling the current to the power source 3, as described above, and the lamp 2 emits light.

After the light adjustment control module 33 performs the process in step S23, the flow returns to the process in step S11. The above-described processes are repeatedly performed until the lamp 2 is shifted to the extinguished state.

Display on the front panel 7 will be described with reference to FIGS. 7 to 9. FIG. 7 is a view showing display on the front panel 7 when the light source apparatus is in an air feeding stopped state and a lamp extinguished state. FIG. 8 is a view showing display on the front panel 7 when the scope is connected, and the light source apparatus is in an air feeding driven state and a lamp lighted state. FIG. 9 is a view showing display on the front panel 7 when the scope is unconnected, and the light source apparatus is to enter the air feeding driven state and the lamp lighted state when the scope is connected. Note that, in FIGS. 7 to 9, each LED is indicated by a white circle if the LED is lighted, is indicated by a black circle if the LED is extinguished, and is indicated by hatching if the LED is blinking.

The lamp switch 41, a lamp STBY LED 42, a lamp ON LED 43, an air feeding switch 44, an air feeding STBY LED 45, an air feeding ON LED 46, and the output connector 47 are provided at the front panel 7.

As described above, the lamp switch 41 is an operation switch for manually lighting the lamp 2.

The lamp STBY LED 42 is an LED for indicating that the lamp 2 is in a standby state waiting for being lighted.

The lamp ON LED 43 is an LED for indicating that the lamp 2 is in the lighted state (a lamp on state).

The air feeding switch 44 is an operation switch for feeding air to a subject via an air feeding channel (not shown) which is provided at the scope 100.

The air feeding STBY LED 45 is an LED for indicating that the light source apparatus is on standby for air feeding.

The air feeding ON LED 46 is an LED for indicating that air feeding is being executed.

The scope 100 is connected to the output connector 47. As will be described later in detail, the output connector 47 has a plurality of connector electric contacts 5 provided inside the output connector 47.

Display on the front panel 7 with the above-described configuration will be described.

When a user performs off operation of the lamp switch 41 and the air feeding switch 44 to put the light source apparatus into the air feeding stopped state and the lamp extinguished state, the lamp STBY LED 42 is lighted, the lamp ON LED 43 is extinguished, the air feeding STBY LED 45 is lighted, and the air feeding ON LED 46 is extinguished, as shown in FIG. 7, regardless of whether the scope 100 is connected or unconnected.

When the scope 100 is connected, and a user performs on operation of the lamp switch 41 and the air feeding switch 44 to put the light source apparatus into the air feeding driven state and the lamp lighted state, the lamp STBY LED 42 is extinguished, the lamp ON LED 43 is lighted, the air feeding STBY LED 45 is extinguished, and the air feeding ON LED 46 is lighted, as shown in FIG. 8.

When the scope 100 is unconnected, and the light source apparatus is to enter the air feeding driven state and the lamp lighted state when the scope 100 is connected, the lamp STBY LED 42 blinks, the lamp ON LED 43 is extinguished, the air feeding STBY LED 45 blinks, and the air feeding ON LED 46 is extinguished, as shown in FIG. 9. That is, when the scope 100 is pulled out and becomes unconnected in the state shown in FIG. 8, the front panel 7 shifts to the state shown in FIG. 9. The display state shown in FIG. 9 is a display state indicating that the front panel 7 shifts to the state shown in FIG. 8 when the scope 100 is connected again. That is, when the scope 100 is connected again in the state shown in FIG. 9, the light source apparatus shifts to the air feeding driven state and the lamp lighted state, of which a user is informed by blinking of the LEDs.

A state in which a standby LED is lighted has conventionally been synonymous with being off. In the case, even if a light source apparatus is set so as to drive air feeding, air feeding is stopped when a scope is unconnected and is automatically driven when the scope is connected. In such a conventional light source apparatus, however, an air feeding ON LED indicating that air feeding is driven remains lighted when a scope is unconnected, which gives an unnatural feeling to a user. As for a lamp, the conventional light source apparatus automatically extinguishes a lamp and lights a lamp STBY LED indicating that the lamp is on standby when the scope is pulled out in a lamp lighted state. When the scope is connected again after the pull-out, the lamp lights automatically, which gives an unnatural feeling to a user.

In contrast, according to the configuration of the present embodiment, a user is informed by blinking of the lamp STBY LED 42 and the air feeding STBY LED 45 that driving of air feeding and lamp lighting are to be automatically performed when the scope 100 is connected. Thus, a conventional unnatural feeling of a user can be eased or eliminated.

In the above-described manner, a user can recognize a lamp lighting state and a pump driving state after connection of the scope, before the scope is connected.

A configuration of the plurality of connector electric contacts 5 disposed in the output connector 47 will be described with reference to FIGS. 12 to 17.

A connection portion 101 (see FIG. 8) on the scope 100 side is configured in, for example, a solid cylindrical shape or a hollow cylindrical shape. The output connector 47, which the connection portion 101 fits on and is connected to, of the light source apparatus 1 also includes an inner surface in a hollow cylindrical shape.

The plurality of connector electric contacts 5 are laid out on the inner surface in a hollow cylindrical shape of the output connector 47 in, for example, a circumferential direction. In recent years, the number of connector electric contacts 5 is increasing, which makes a spacing between the adjacent connector electric contacts 5 relatively narrow.

Figure 12:
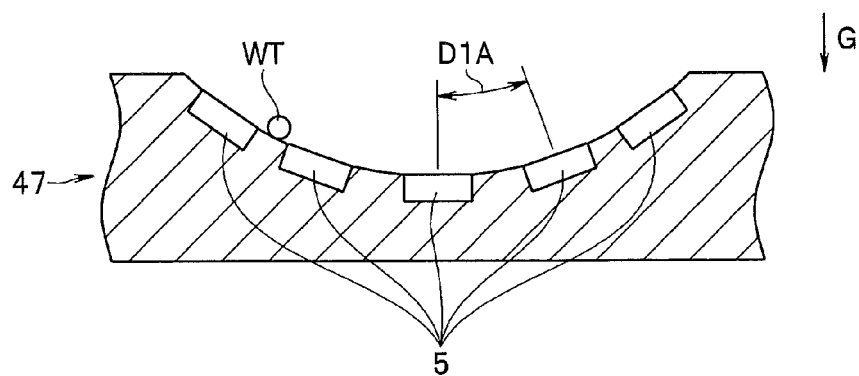
FIG. 12 is a view showing a general layout of a plurality of connector electric contacts at an output connector, in association with the first embodiment.
Figure 13:
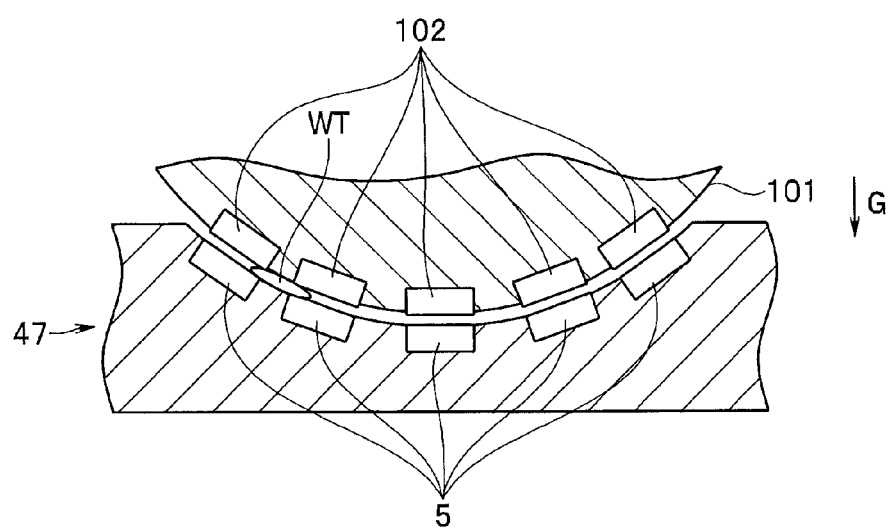
FIG. 13 is a view showing how the connector electric contacts and endoscope-side electric contacts are when a connection portion of a scope is connected to the general output connector, in association with the first embodiment.

A general layout of electric contacts will be described first with reference to FIGS. 12 and 13. FIG. 12 is a view showing a general layout of a plurality of connector electric contacts 5 at the output connector 47. FIG. 13 is a view showing how the connector electric contacts 5 and endoscope-side electric contacts 102 are when the connection portion 101 of the scope is connected to the general output connector 47.

The front panel 7 is generally arranged such that a front face faces in a vertical direction (i.e., a normal to the front face faces in a horizontal direction). Thus, some of the connector electric contacts 5 are arranged on an upper side in a direction of gravitational force, and some are arranged on a lower side in the direction of gravitational force, in the output connector 47. FIGS. 12 and 13 show how the connector electric contacts 5 arranged on the lower side in the direction of gravitational force of the connector electric contacts 5 are (an arrow G indicates the direction of gravitational force).

The scope 100 is cleaned, disinfected, and sterilized after each use. In a normal situation, the scope 100 is used next time after the scope 100 is sufficiently dried after the processing. However, a user may use the scope 100 next time before sufficient drying ends. A conductive liquid WT (e.g., water) used for processing such as cleaning may adhere to a neighborhood of the connector electric contact 5. In addition to the example, the conductive liquid WT may adhere to the output connector 47. The liquid WT often goes to a neighborhood of the connector electric contact 5 arranged on the lower side in the direction of gravitational force by dropping or moving down.

Even if the amount of liquid WT is small, as shown in FIG. 12, when the connection portion 101 of the scope 100 is connected to the output connector 47, the liquid WT may spread astride the adjacent connector electric contacts 5 due to capillarity, as shown in FIG. 13, and the connector electric contacts 5 may be bridged with the liquid WT.

Figure 14:
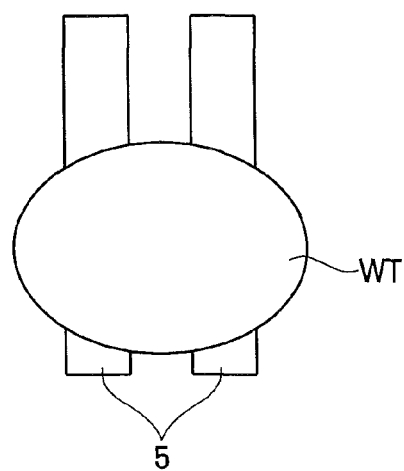
FIG. 14 is a view showing a state in which two adjacent connector electric contacts are bridged with conductive liquid, according to the first embodiment.

FIG. 14 is a view showing a state in which two adjacent connector electric contacts 5 are bridged with the conductive liquid WT.

Figure 15:
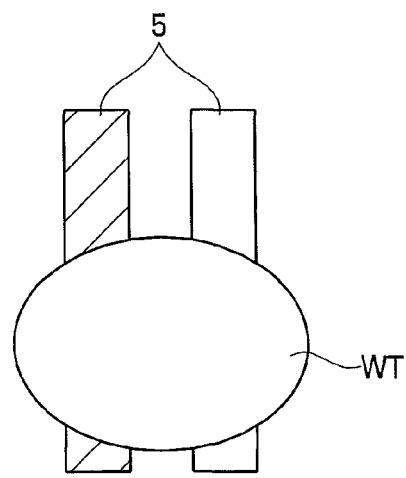
FIG. 15 is a view showing a state in which electrolytic corrosion has occurred in one of the two connector electric contacts bridged with the conductive liquid, according to the first embodiment.

When the connector electric contacts 5 are energized in the state, if there is a potential difference between the connector electric contacts 5, electrolytic corrosion may occur at the connector electric contact 5 at a lower potential, as indicated by the hatched portion in FIG. 15. FIG. 15 here is a view showing a state in which electrolytic corrosion has occurred in one of the two connector electric contacts 5 bridged with the conductive liquid WT. Occurrence of such electrolytic corrosion may lead to a problem, such as occurrence of an abnormality in an image transmitted via the connector electric contacts 5.

Figure 16:
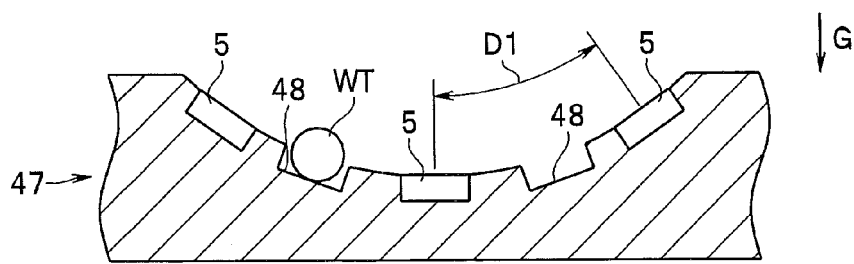
FIG. 16 is a view showing a layout of a plurality of connector electric contacts at an output connector according to the first embodiment.
Figure 17:
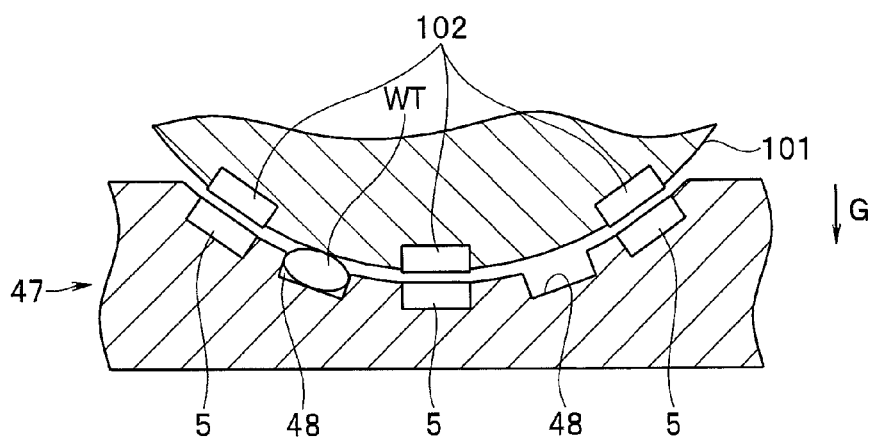
FIG. 17 is a view showing how the connector electric contacts and the endoscope-side electric contacts are when a connection portion of the scope is connected to the output connector, according to the first embodiment.

Under the circumstances, in the present embodiment, the configuration as shown in FIGS. 16 and 17 is adopted instead of the configuration as shown in FIGS. 12 and 13. Here, FIG. 16 is a view showing a layout of a plurality of connector electric contacts 5 at the output connector 47 according to the present embodiment. FIG. 17 is a view showing how the connector electric contacts 5 and the endoscope-side electric contacts 102 are when the connection portion 101 of the scope is connected to the output connector 47 according to the present embodiment.

As a first electrolytic corrosion prevention technique, a contact-to-contact distance D1 on the lower side in the direction of gravitational force of the connector electric contacts 5 shown in FIG. 16 is set to be longer than a contact-to-contact distance D1A of the general connector electric contacts 5 shown in FIG. 12. If the total number of connector electric contacts 5 laid out in the circumferential direction in the output connector 47 is not changed, contact-to-contact distances on the upper side (not shown) in the direction of gravitational force and on lateral sides (not shown) in the direction of gravitational force are smaller than the contact-to-contact distance D1 and are also smaller than the contact-to-contact distance D1A.

As described above, there is no significant difference in contact-to-contact distance between on an upper side in a direction of gravitational force and on a lower side in a general output connector. In contrast, in the output connector 47 according to the present embodiment, the contact-to-contact distance D1 on the lower side in the direction of gravitational force where liquid having intruded into the connector is likely to be left is set to be longer than the contact-to-contact distances on the upper side in the direction of gravitational force and on the lateral sides in the direction of gravitational force where liquid is unlikely to be left.

The above-described configuration allows reduction in the frequency of occurrence of a liquid bridge between the connector electric contacts 5 which leads to electrolytic corrosion and, by extension, reduction in electrolytic corrosion.

Additionally, as a second electrolytic corrosion prevention technique, a concave portion 48 is provided at a position between the connector electric contacts 5 laid out on the lower side in the direction of gravitational force in the output connector 47 shown in FIG. 16. Note although that one concave portion 48 is provided between each adjacent two of the connector electric contacts 5 in the example shown in FIGS. 16 and 17, a plurality of concave portions 48 may be provided.

With the provision of the concave portion 48, a place where the liquid WT is held is produced when the connection portion 101 of the scope 100 is connected to the output connector 47 (the liquid WT has a high chance of being wholly held if the liquid WT is small, as shown in FIG. 17), and occurrence of expansion and spread of the liquid WT due to capillarity can be inhibited. Additionally, since a creepage distance between the adjacent connector electric contacts 5 is longer, even if capillarity occurs, the frequency with which the expanding and spreading liquid WT becomes a liquid bridge lying astride two connector electric contacts 5 can be reduced. The reduction allows reduction in electrolytic corrosion.

Note that although the concave portion 48 is provided in the above description, the present invention is not limited to the configuration. A through-hole (drip hole) which penetrates to an outside of a housing may be constructed. Note that if the liquid WT is water, the through-hole is desirably formed to be as large as possible in consideration of high surface tension.

In addition, as a third electrolytic corrosion prevention technique, the connector electric contacts 5 laid out on the lower side in the direction of gravitational force are arranged so as to minimize a potential difference between the adjacent connector electric contacts 5. That is, electrolytic corrosion at the connector electric contacts 5 bridged with the conductive liquid WT makes rapider progress as a potential difference between the connector electric contacts 5 becomes large. For the reason, electrolytic corrosion is inhibited by minimizing the potential difference and reducing the potential difference to a potential difference which allows electrolytic corrosion to make little progress (e.g., a potential difference of not more than about 1 V).

The above-described first to third electrolytic corrosion prevention techniques may be appropriately combined. For example, a design is first made so as to minimize a potential difference between the adjacent connector electric contacts 5. Note that if the potential difference between the adjacent connector electric contacts 5 is inevitably large in terms of design, a contact-to-contact distance at the portion is lengthened as much as possible, and a concave groove or a through-hole is provided.

Figure 18:
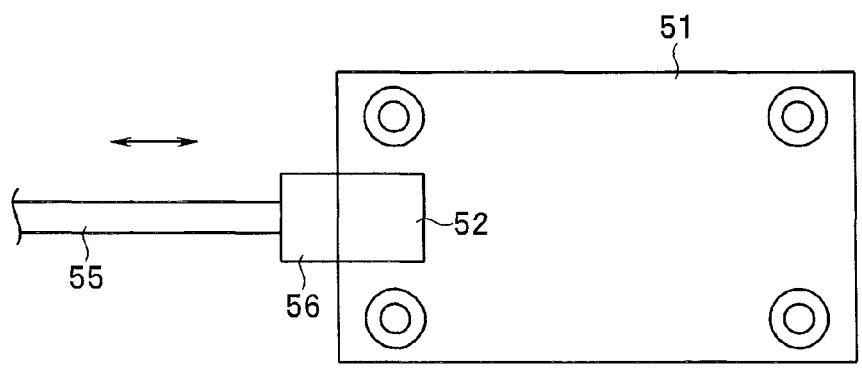
FIG. 18 is a view showing a general structure in which a board and a harness are connected, in association with the first embodiment.
Figure 19:
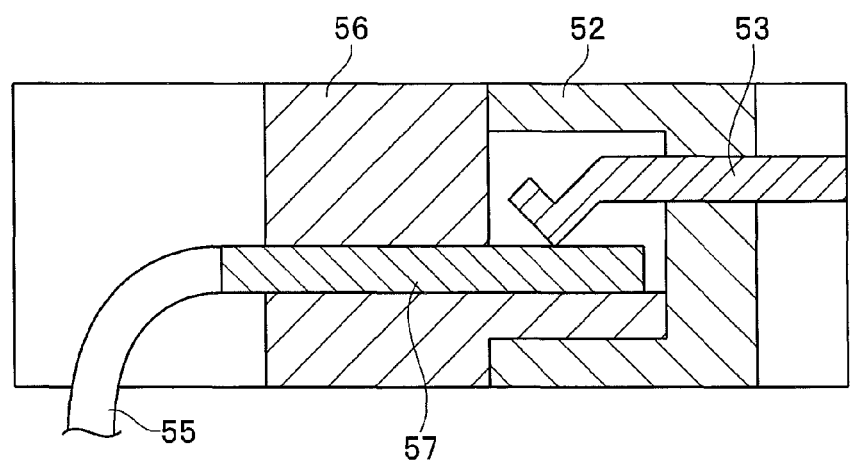
FIG. 19 is a cross-sectional view showing a structure in which the harness and a board-side connector are connected, in association with the first embodiment.
Figure 20:
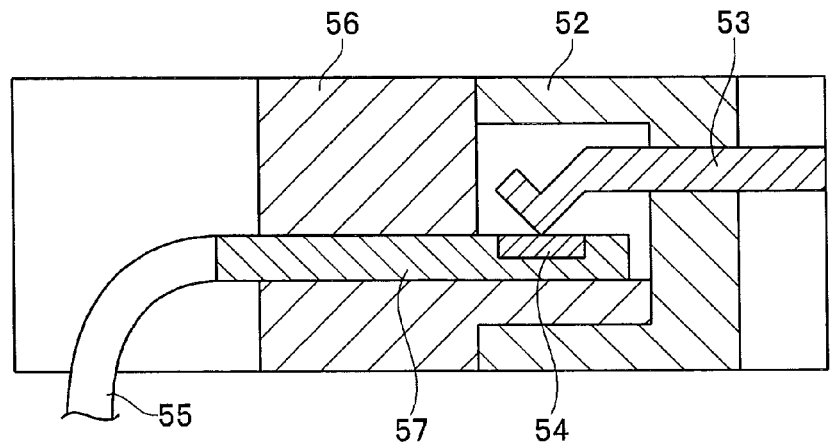
FIG. 20 is a cross-sectional view showing a state in which an oxide film is produced between a harness-side terminal and a board-side terminal, in association with the first embodiment.
Figure 21:
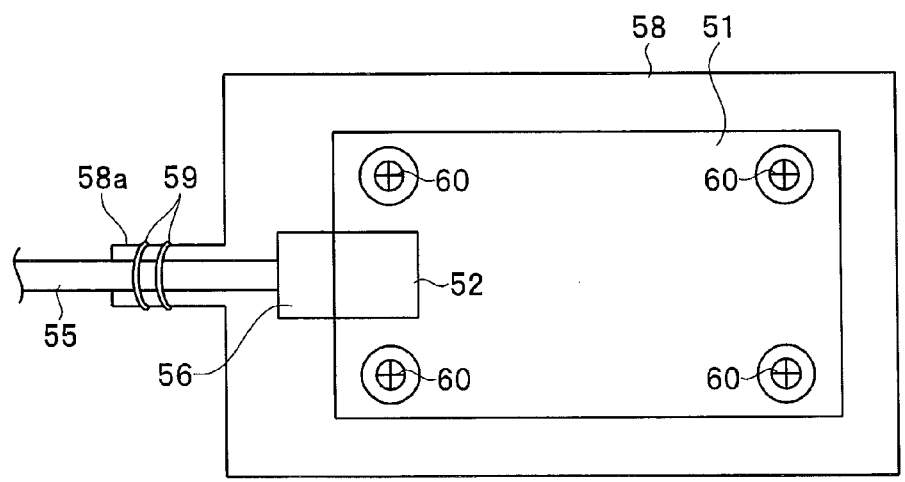
FIG. 21 is a view showing a structure in which a board and a harness are connected according to the first embodiment.

A connection structure for a board in the light source apparatus 1 will be described with reference to FIGS. 18 to 21. FIG. 18 is a view showing a general structure in which a board and a harness are connected. FIG. 19 is a cross-sectional view showing a structure in which the harness and a board-side connector are connected. FIG. 20 is a cross-sectional view showing a state in which an oxide film is produced between a harness-side terminal and a board-side terminal. FIG. 21 is a view showing a structure in which a board and a harness are connected according to the present embodiment.

A plurality of electrical circuit boards are provided in the light source apparatus 1. Some of the boards, however, may not be completely fixed to a main body of the light source apparatus 1 and may be floating or be configured to be capable of moving somewhat (some examples of the boards are a board provided with the connector electric contacts 5, to which the above-described scope 100 is to be connected, and the scope sensing board 6).

A movable board 51 as described above is configured so as to be electrically connected to a different circuit by connecting a board-side connector 52 to a harness-side connector 56 of a harness 55, as shown in FIG. 18.

A connection between the board-side connector 52 and the harness-side connector 56 is configured such that a harness-side terminal 57 which is extended from the harness-side connector 56 side touches and is electrically connected to a board-side terminal 53 which is provided at the board-side connector 52, as shown in, for example, FIG. 19.

However, repetitive movement of the board 51 and the harness 55 relative to each other (due to, e.g., application of vibrations) may cause wear at the connection between the harness-side terminal 57 and the board-side terminal 53 to form an oxide film 54, as shown in FIG. 20. The oxide film 54 may make electrical continuity between the terminals difficult.

For the reason, a fixing member 58 for integrally fixing the board 51 and the harness 55 is provided in the present embodiment, as shown in FIG. 21.

The fixing member 58 includes a main body part which can contact the board 51 and an extending part 58a which can contact the harness 55. The fixing member 58 is fixed to the movable board 51 at the main body part by screwing, for example, screws 60 and is fixed to the harness 55 at the extending part 58a by fastening a bind 59.

With the above-described configuration, even if vibrations are applied to either the board 51 or the harness 55, the board 51 and the harness 55 vibrate integrally, and relative displacement is prohibited, which inhibits wear of the connection part between the harness-side terminal 57 and the board-side terminal 53. The inhibition prevents formation of an oxide film at the connection part between the harness-side terminal 57 and the board-side terminal 53 and allows securement of electrical continuity between the terminals with high reliability.

According to the first embodiment described above, a continuous lighting time period during which a lighted state is maintained without interruption, is measured from a time point when a light source portion shifts from an extinguished state to the lighted state, control is performed such that an upper limit power is a first upper limit power when the continuous lighting time period is not sensed to have reached an upper limit time period, and control is performed such that the upper limit power is a second upper limit power lower than the first upper limit power when the continuous lighting time period is sensed to have reached the upper limit time period. Thus, a phenomenon in which light emission luminance of a lamp becomes unstable and a phenomenon in which a light emission spectrum of the lamp changes can be avoided, which allows stable long-time emission of light with as high light emission luminance as possible.

Additionally, a change from the first upper limit power to the second upper limit power when the continuous lighting time period is sensed to have reached the upper limit time period is made in a stepwise manner in decrements smaller than a power difference between the first upper limit power and the second upper limit power. Thus, the light source portion can shift to a state which prevents occurrence of a flicker and a color shift of the lamp while preventing a change in brightness of light from the lamp from giving an unnatural feeling to a user.

Note that although a light source apparatus has been mainly described above, the present invention may be applied to a control method for controlling a light source apparatus in the above-described manner, a control program for causing a computer to control a light source apparatus in the above-described manner, a computer-readable recording medium having the control program recorded, and the like.

The present invention is not limited to just the embodiment described above and can be embodied by modifying constituent elements without departing from spirit of the invention in an implementation stage. Additionally, various aspects of the invention can be formed by appropriately combining the plurality of constituent elements disclosed in the embodiment. For example, some constituent elements may be deleted from all constituent elements shown in the embodiment. In addition, constituent elements of different embodiments may be appropriately combined. As described above, various modifications and applications can, of course, be made without departing from scope of the invention.

What is claimed is:

1. A light source apparatus for an endoscope comprising:
a light source portion that can have a lighted state in which light is generated and an extinguished state in which no light is generated;
a power supply portion that supplies power for the light source portion to generate light in the lighted state;
an outgoing light amount control portion that controls an amount of outgoing light from the light source portion by controlling power to be supplied to the light source portion by the power supply portion within a range not more than an upper limit power based on an inputted brightness instruction signal; and
a continuous lighting sensing portion that measures a continuous lighting time period during which the lighted state is maintained without interruption, from a time point when the light source portion shifts from the extinguished state to the lighted state and senses whether the continuous lighting time period has reached a predetermined upper limit time period, and initializes the continuous lighting time period within a period during which the light source portion is in the extinguished state,
wherein the outgoing light amount control portion performs power supply control to the light source portion based on the brightness instruction signal with the upper limit power set to a first upper limit power when the continuous lighting time period is not sensed to have reached the upper limit time period, performs power supply control to the light source portion based on the brightness instruction signal with the upper limit power set to a second upper limit power lower than the first upper limit power when the continuous lighting time period is sensed to have reached the upper limit time period, and performs control to make a change from the first upper limit power to the second upper limit power when the continuous lighting time period is sensed to have reached the upper limit time period in a stepwise manner in decrements each smaller than a power difference between the first upper limit power and the second upper limit power.

2. A control method for a light source apparatus for an endoscope, comprising:
shifting a light source portion from an extinguished state in which no light is generated to a lighted state in which light is generated by supplying power to the light source portion;

measuring a continuous lighting time period during which the lighted state is maintained without interruption, from a time point when the light source portion shifts from the extinguished state to the lighted state;

sensing whether the continuous lighting time period has reached a predetermined upper limit time period;

controlling power to be supplied to the light source portion based on an inputted brightness instruction signal with an upper limit power which serves as an upper limit for the power to be supplied to the light source portion set to a first upper limit power when the continuous lighting time period is not sensed to have reached the upper limit time period;

controlling the power to be supplied to the light source portion based on the brightness instruction signal with the upper limit power that serves as the upper limit for the power to be supplied to the light source portion set to a second upper limit power lower than the first upper limit power when the continuous lighting time period is sensed to have reached the upper limit time period, and controlling a change from the first upper limit power to the second upper limit power when the continuous lighting time period is sensed to have reached the upper limit time period, to be performed in a stepwise manner in decrements each smaller than a power difference between the first upper limit power and the second upper limit power; and initializing the continuous lighting time period within a period during which the light source portion is in the extinguished state.

* * * * *